(12) United States Patent
Zheng et al.

(10) Patent No.: US 7,124,636 B2
(45) Date of Patent: Oct. 24, 2006

(54) NON-CONTACT MEASUREMENT OF MATERIAL PROPERTY

(75) Inventors: Yongping Zheng, Kowloon (CN); Minhua Lu, Kowloon (CN)

(73) Assignee: The Hong Kong Polytechnic University, Hong Kong (CN)

( * ) Notice: Subject to any disclaimer, the term of this patent is extended or adjusted under 35 U.S.C. 154(b) by 43 days.

(21) Appl. No.: 10/954,022

(22) Filed: Sep. 30, 2004

(65) Prior Publication Data

US 2006/0065056 A1 Mar. 30, 2006

(51) Int. Cl.
*G01N 29/00* (2006.01)
(52) U.S. Cl. ......................................... 73/649; 644/807
(58) Field of Classification Search .................. 73/649, 73/800, 806, 807, 644, 671; 600/552, 587
See application file for complete search history.

(56) References Cited

U.S. PATENT DOCUMENTS

| | | | |
|---|---|---|---|
| 5,265,612 A * | 11/1993 | Sarvazyan et al. | 600/471 |
| 5,582,171 A * | 12/1996 | Chornenky et al. | 600/425 |
| 5,678,565 A * | 10/1997 | Sarvazyan | 600/587 |
| 6,280,960 B1 * | 8/2001 | Carr | 435/7.2 |
| 6,338,443 B1 * | 1/2002 | Piper | 239/340 |
| 6,783,503 B1 | 8/2004 | Duda et al. | 600/587 |
| 6,951,131 B1 * | 10/2005 | Sawert et al. | 73/290 V |

OTHER PUBLICATIONS

Abstract of presentation at Second International Conference on Ultrasonic Measurement and Imaging of Tissue . . . , Oct. 12-15, 2003.

* cited by examiner

*Primary Examiner*—Hezron Williams
*Assistant Examiner*—Jacques Saint-Surin
(74) *Attorney, Agent, or Firm*—Jacobson Holman PLLC

(57) ABSTRACT

A process for measuring a property of a sample is provided. The sample has an external surface enclosing an inner portion, and firstly, the sample is deformed by applying a predetermined non-contact pressure to deform a portion of the sample. Then a signal, which is at least suitable for transmission over the air, is directed towards the deformed portion of the sample, and further propagates through the external surface and the inner portion of the sample. Then an echoed signal generated by the inner portion of the sample in response to the propagation of the signal is detected; wherein the echoed signal incorporates information relating to a deformation of the inner portion of the sample. The property of the sample is determined from the deformation of the inner portion of the sample.

19 Claims, 3 Drawing Sheets

FIG. 2A
FIG. 2B
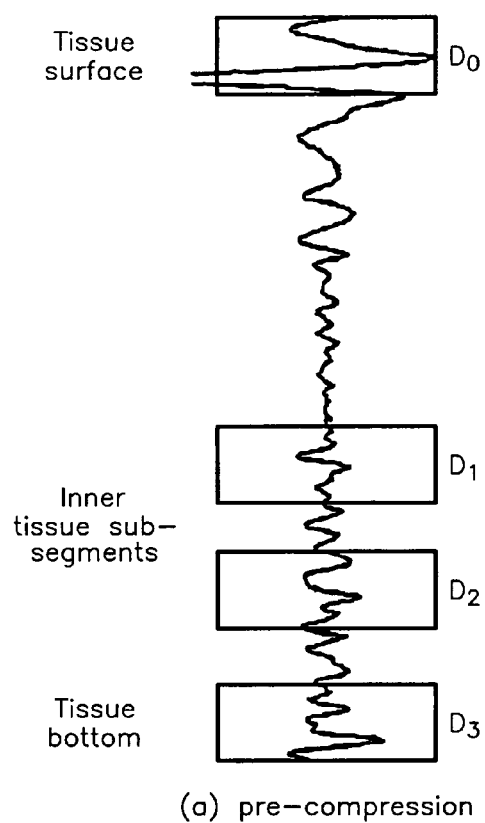
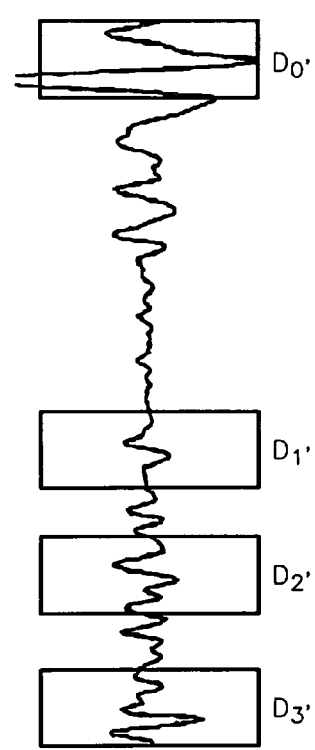
(a) pre-compression
(b) post-compression

NON-CONTACT MEASUREMENT OF MATERIAL PROPERTY

BACKGROUND

1. Field of the Invention

The present invention relates to technologies for measuring the properties of materials such as biological tissues or engineering materials without the measurement apparatus being in contact with the samples.

2. Background of the Invention

Conventionally, mechanical properties of materials such as biological tissues or engineering materials are measured by using a testing probe to contact the samples for the measurement. In such a conventional measurement, it may be difficult to quickly image an area larger than the probe in that the probe needs to be loaded and unloaded repeatedly, which can be time-consuming.

U.S. Pat. No. 6,783,503, entitled "Method and Device for Testing the Rigidity of Biological Tissue" and assigned to Karl Storz, GmbH & Co. KG, discloses a contact-free measurement of the mechanical rigidity of a biological sample. Specifically, the sample is deformed by a jet of fluid, and the deformation is detected by optically measuring the distance between the measuring surface and the measuring device.

Disadvantages exist with the design of the '503 patent in that firstly, it failed to consider the thickness of the sample, which may affect the deformation of the sample and consequently the measurement of the mechanical rigidity of the biological sample. Furthermore, the optical distance measurement of the '503 patent merely provides limited information, i.e., the distance between the measuring surface and the measuring device, about the sample, which may not be satisfactory in a situation, where more complicated information is required.

OBJECT OF THE INVENTION

Therefore, it is an object of the present invention to provide a more accurate measurement of the mechanical properties of a sample, which may also provide more property information about the sample, or at least provide the public with a useful choice.

SUMMARY OF THE INVENTION

According to an aspect of the present invention, a process for measuring a property of a sample is provided. The sample has an external surface enclosing an inner portion, and firstly, the sample is deformed by applying a predetermined non-contact pressure to deform a portion of the sample. Then a signal, which is at least suitable for transmission over the air or water, is directed towards the deformed portion of the sample, and further propagates through the external surface and the inner portion of the sample. Then an echoed signal generated by the inner portion of the sample in response to the propagation of the signal is detected; wherein the echoed signal incorporates information relating to a deformation of the inner portion of the sample. The property of the sample is determined from the deformation of the inner portion of the sample.

According to another aspect of the present invention, an apparatus for determining a property of a sample, wherein the sample has an external surface enclosing an inner portion, comprises a pressure generator distanced from the sample for generating a predetermined non-contact pressure on the sample to deform a portion of the sample;

a signal emitter for directing a signal towards the deformed portion of the sample, wherein the signal is at least suitable for transmission over the air or water and suitable for propagating through the inner portion of the sample;

a signal detector for detecting an echoed signal generated by the inner portion of the sample in response to the propagation of the signal, wherein the echoed signal incorporates information relating to a deformation of the inner portion of the sample; and a processor for processing the echoed signal to determine the property of the sample from the deformation of the inner portion of the sample.

Other aspects and advantages of the invention will become apparent from the following detailed description, taken in conjunction with the accompanying drawings, which description illustrates by way of example the principles of the invention.

BRIEF DESCRIPTION OF THE DRAWINGS

FIGS. 2A and 2B illustrate measured signals by the apparatus of FIG. 1; and

DETAILED DESCRIPTION

Figure 1:
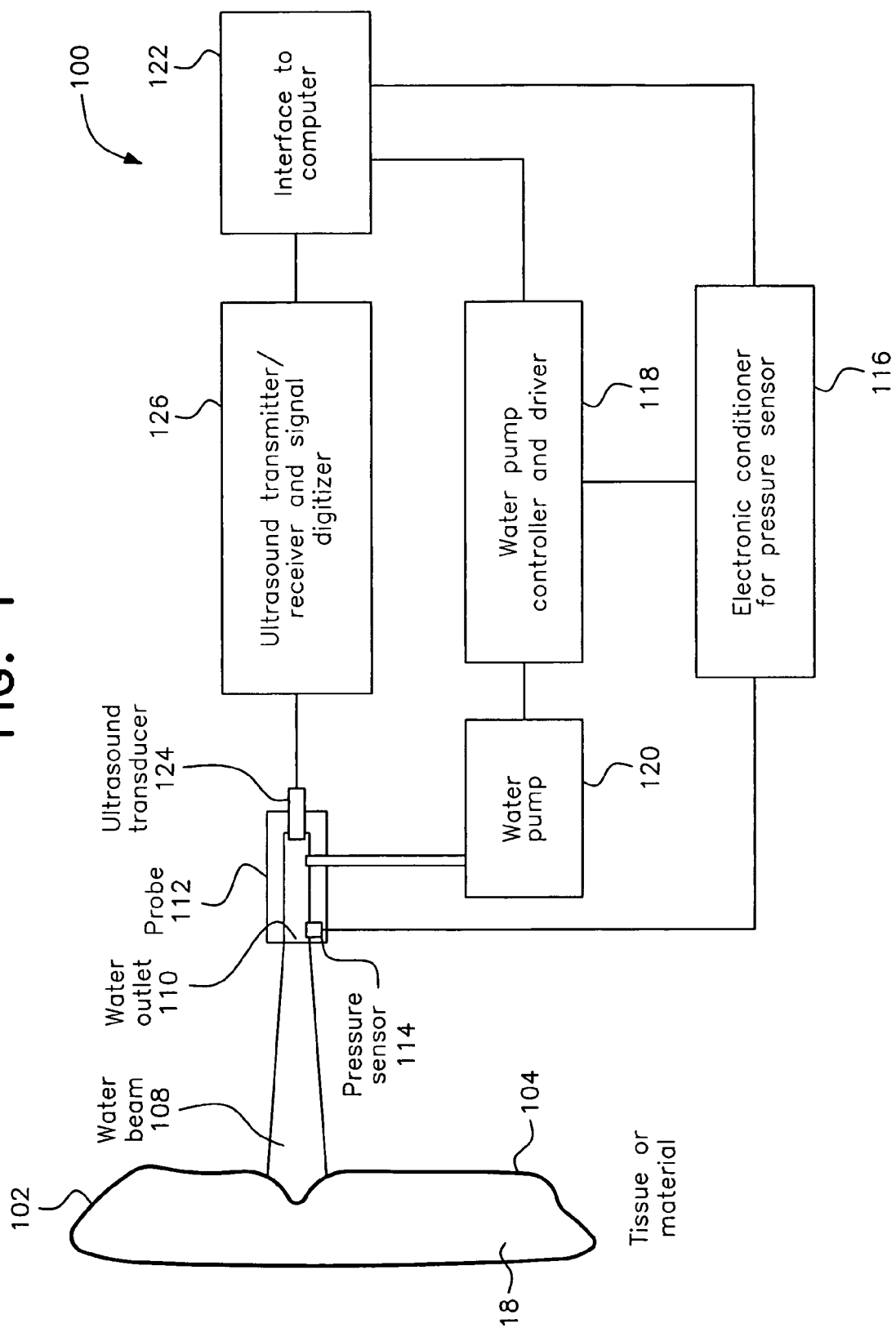
FIG. 1 is a diagram illustrating a non-contact measurement apparatus according to an exemplary embodiment of the present invention.

FIG. 1 Illustrates a non-contact measurement apparatus 100 according to an exemplary embodiment of the present invention for determining a property for example the elasticity of a sample 102 such as biological tissues or engineering materials. The sample 102 has an external surface 104 enclosing an inner portion 106, and at least part of the external surface 104 faces the measurement apparatus 100. A water beam 108 of a predetermined pressure is ejected from a water outlet 110 incorporated in a probe 112 of the measurement apparatus 100 towards the sample 102 such that the sample 102 is compressed under the pressure of the water beam 108 and thereby deformed to an extent in accordance with the pressure. A pressure sensor 114, in close proximity to the exit (not shown) of water outlet 110, senses the pressure of the water beam 108 and feeds such information to an electronic conditioner 116, which is in connection with a water pump controller and driver 118 for controlling a water pump 120 to generate the water beam 108 of the predetermined pressure. Both the electronic conditioner 116 and the water pump controller and driver 118 are in connection with an interface 122 for connecting to a computer (not shown), to which the measurement apparatus 100 can be connected for processing. Furthermore, in the probe 112, an ultrasound transducer 124 is provided for emitting ultrasonic signals towards the sample 102 for the measurement purposes, which will be discussed in details below. An ultrasound transmitter/receiver and signal digitizer 126, in connection with the ultrasound transducer 124, works with the ultrasound transducer 124 for generating the ultrasonic signals and detects echoed ultrasonic signals from the sample 102 for the measurement. The transmitter/receiver and signal digitizer 126 also transmits the received echoed ultrasonic signals to the computer through the interface 122 for processing. It can be understood that the measurement apparatus 100 may include a processor and a display to replace the computer for the processing of the received echoed ultrasonic signals and for display of the processing result.

In the exemplary embodiment of FIG. 1, the sample 102 is deformed under the compression of the water beam 108. As could be understood by the people in the art, both the external surface 108 and the inner portion 106 of the sample 102 are deformed under such compression. The exemplary embodiment measures both deformations to provide a more accurate measurement of the elasticity or other mechanical properties of the sample 102 and may also reveal more property information of the sample 102.

As could be understood by the person in the art, ultrasonic signals can propagate through the biological tissues or materials. In the exemplary embodiment of FIG. 1, the ultrasound transmitter/receiver 126 detects reflected ultrasonic signals echoed from both the external surface 104 and the inner portion 106 of the sample 102, which echoes or reflections are in response to the propagation of the ultrasonic signals through the sample 102. Thus, by analyzing the echoed signals, in addition to the overall deformation of the sample 102, the present invention can also determine the deformation of each inner part of the tissue under this pressure. In this way, a more accurate measurement of the deformation of the biological sample can be achieved.

As illustrated in FIGS. 2A and 2B, the exemplary measurement apparatus 100 executes two steps to measure the elasticity of the sample 100. Firstly, the sample is not compressed, and the measurement apparatus 100 detects a set of echoed ultrasonic signals from both the external surface 104 and various layers or inner portions of the sample. This set of ultrasonic signals is used as the reference signals. D0 represents the reference point and can be the original surface of the sample. D1–D3 can be calculated from the propagation time of the ultrasonic waves from the reference position to the interested region and the corresponding propagation speed in the sample.

In the second step, the sample is compressed by the water beam of a predetermined pressure, and another set of echoed ultrasonic signals is obtained for measuring the deformation of the sample 100 under such a pressure. D0'–D4' are also obtained similar to the D0–D4.

By comparing the two sets of ultrasonic signals, deformations of the inner portion 106 can be determined. Specifically, if only the surface displacement is concerned, only the signal from the tissue surface needs to be tracked. Under the assumption that the tissue bottom does not move during the compression, the overall deformation of the sample can be estimated as $D_0'-D_0$. The sample thickness cannot be obtained by only tracking the tissue surface. By using the ultrasonic signals, in addition to the sample surface, the movement of the sample bottom can also be monitored. Hence, the original sample thickness can be calculated as $D_3-D_0$. The overall sample deformation can be more accurately calculated as $(D_3'-D_0')-(D_3-D_0)$, with the consideration of the movement of the sample bottom. The relative deformation, i.e. the strain, can also be obtained, which can better describe the sample deformation under certain pressure, as the thickness effect has been taken into account. The strain is $[(D_3'-D_0')-(D_3-D_0)]/(D_3-D_0)$. By dividing the applied pressure by the deformations or the strain, the stiffness values of the sample can be calculated. As could be understood, the ratio of the pressure and the strain can better represent the sample elasticity.

FIGS. 2A and 2B also illustrate how the elasticity of the inner portions of the sample can be obtained. $D_1$ and $D_2$ represent the original positions of two sub-segments of the sample. After compression, they moved to $D_1'$ and $D_2'$, respectively. The strain of the portion of inter sample is $[(D_2'-D_1')-(D_2-D_1)]/(D_2-D_1)$. The ratio of the applied pressure and the strain represents the sample stiffness. Similar method can be applied to other portions of the sample to get their stiffness.

Since the pressure distribution can be different at different parts of the sample in the lateral as well as the axial direction. A computer simulation can be conducted to obtain the pressure distribution based on the obtained overall deformation of the sample, the overall applied force, as well as the sample thickness. Hence, a more accurate estimation of the stiffness for a sample portion at certain position can be conducted based on the simulated pressure at that position A more advanced method is to obtain the stiffness of the sample by solving an inverse problem, i.e. the stiffness distribution is calculated from the measured strain distribution, the applied force, and the tissue thickness by using a numerical optimization procedure to achieve a minimal estimation error. In addition, it can be understood that the exemplary embodiment can be used to obtain a two-dimensional profile of the compressed area of the sample.

Furthermore, more accurate measurement can be achieved by averaging the measurement results obtained at different levels of pressures of the water beam. Also, non-linear property of the sample under different pressures can thereby be obtained. In addition, the viscoelastic properties can be obtained by monitoring the transient tissue deformation under a constant pressure, the change of the pressure required to maintain a constant deformation, or the phase shift between the cyclic deformation induced by a cyclically changing pressure.

Figure 3:
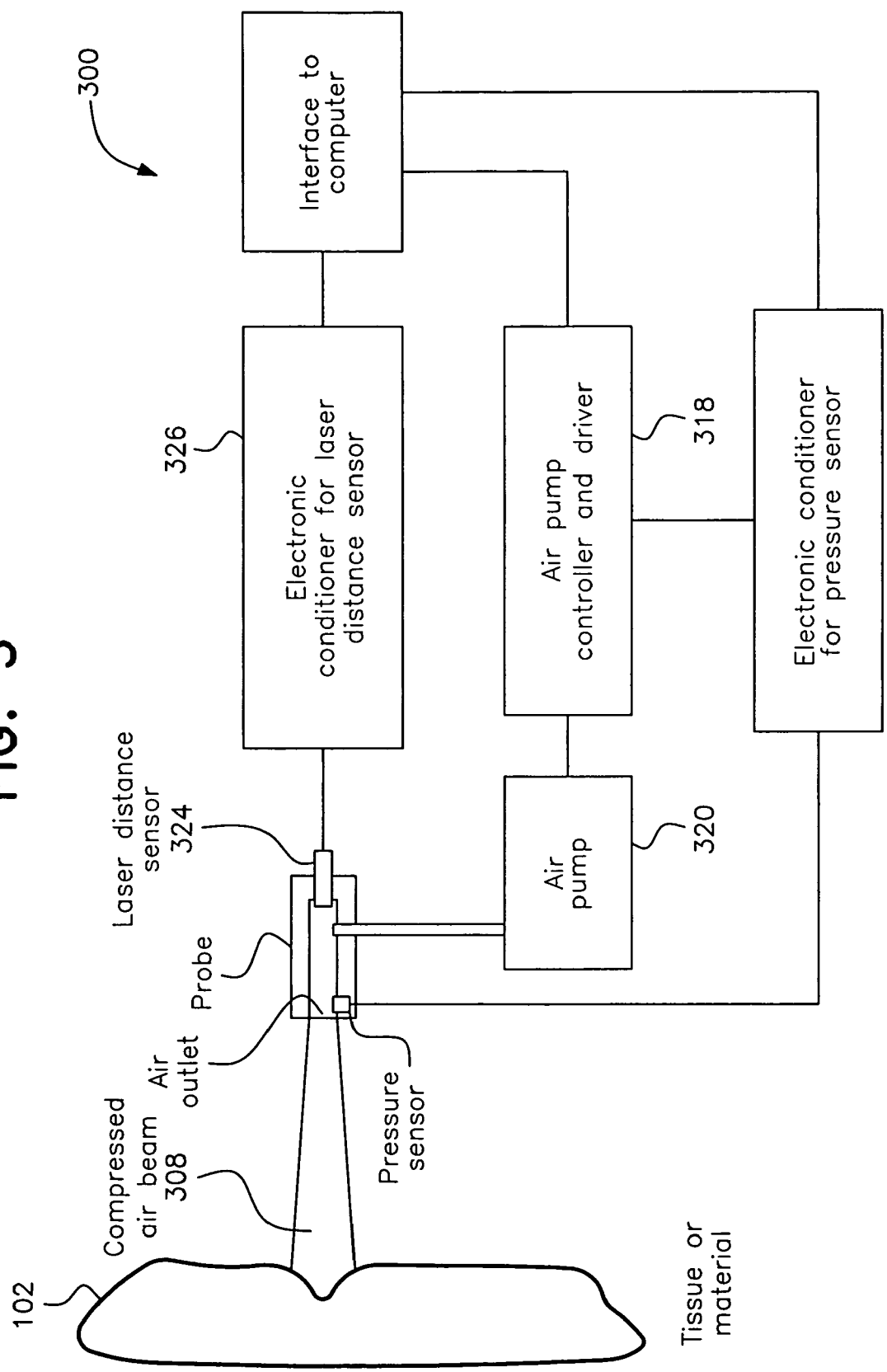
FIG. 3 is a diagram illustrating a non-contact measurement apparatus according to another exemplary embodiment of the present invention.

FIG. 3 illustrates another embodiment of the present invention. Instead of the water beam 108 of the embodiment of FIG. 1, in FIG. 3, the measurement apparatus 300 uses an air pump 320 and an air pump controller and driver 318 to generate a compressed air beam 308 of a predetermined pressure for deforming the sample. In addition, the apparatus 300 uses a laser distance sensor 324 and an electronic conditioner for laser distance sensor 326 to optically detect the deformation of the sample. Instead of traditional optical signals, the apparatus 300 uses optical coherence tomography method, which uses low-coherence interferometry to produce optical scattering from internal sample microstructure along the depth direction in a way that is analogous to ultrasonic pulse-echo imaging. When a pressure is applied on the soft sample using an air or water pressure, the deformations of sample layers at different depths can be obtained from the movement of the optical scattering signals. In addition, the optical detection can also be optical confocal microscopy, which can detect the surface of a tissue but also its superficial layers.

When a water beam is used to deformation the tissue of a living body or a specimen, the water may split around. A vacuum suction probe beside the water beam can be used to collect the water after it splits form the tissue.

What is claimed is:

1. A process for measuring a property of a sample having an external surface enclosing an inner portion, comprising:
    ejecting a jet of fluid, compressed aerosol, laser beam, electron beam or focused acoustic beam onto the external surface of the sample to obtain deformation of a portion of the sample;

directing a signal towards the deformed portion of the sample, wherein the signal is at least suitable for non-contact transmission;

propagating the signal through the external surface and inside the inner portion of the sample;

detecting an echoed signal generated by the inner portion of the sample in response to the propagation of the signal, wherein the echoed signal incorporates information being indicative of a deformation of the inner portion of the sample; and determining the property of the sample from the deformation of at least the inner portion of the sample.

2. The process of claim 1, wherein the signal is an ultrasonic signal suitable for propagating through the inner portion of the sample.

3. The process of claim 1, wherein the signal is an optical signal, and wherein the process further comprising propagating the optical signal through the inner portion of the sample by using optical coherence tomography technology.

4. The process of claim 1, wherein the signal is an optical signal, and wherein the process further comprising propagating the optical signal through the inner portion of the sample by using confocal technique.

5. The process of claim 1, further comprising varying the predetermined pressure to vary the deformation of the sample; and determining the property of the sample from the deformations of the sample under the different pressures.

6. The process of claim 1, further comprising maintaining the predetermined pressure for a period to cause the change of the deformation of the sample; and determining the viscoelastic property of the sample from the time-dependent deformations of the sample.

7. The process of claim 1, further comprising varying the predetermined pressure cyclically to vary the deformation of the sample; and determining the viscoelastic property of the sample from phase difference between the deformation and the pressure.

8. The process of claim 1, wherein the property relates to elasticity of the sample.

9. The process of claim 1, wherein the property relates to viscoelasticity of the sample.

10. An apparatus for determining a property of a sample having an external surface enclosing an inner portion, comprising a pressure generator for placement at a distance from the sample, the pressure generator ejecting a jet of fluid, compressed aerosol, laser beam, electron beam or focused acoustic beam onto the external surface of the sample to obtained deformation of a portion of the sample;

a signal emitter for emitting a signal towards the deformed portion of the sample, wherein the signal is at least suitable for non-contact transmission and at least suitable for propagating through the inner portion of the sample;

a signal detector for detecting a signal echoed by the inner portion of the sample in response to the propagation of the signal, wherein the echoed signal incorporates information being indicative of a deformation of the inner portion of the sample; and a processor for processing the echoed signal to determine the property of the sample from the deformation of the inner portion of the sample.

11. The apparatus of claim 10, wherein the signal is an ultrasonic signal suitable for propagating inside the inner portion of the sample.

12. The apparatus of claim 10, wherein the signal is an optical signal, and wherein the apparatus further comprising an optical coherence tomography mechanism for assisting propagation of the optical signal inside the inner portion of the sample.

13. The apparatus of claim 10, wherein the signal is an optical signal, and wherein the apparatus further comprising an optical confocal mechanism for assisting propagation of the optical signal inside the inner portion of the sample.

14. The apparatus of claim 10, further comprising a pressure regulator for varying the predetermined pressure to vary the deformation of the sample, wherein the processor determines the property of the sample from the deformations of the sample under the different pressures.

15. The apparatus of claim 10, wherein the property relates to elasticity of the sample.

16. The apparatus of claim 10, wherein the property relates to viscoelasticity of the sample.

17. The apparatus of claim 10, wherein the pressure generator includes a fluid ejector for ejecting a jet of fluid towards the sample.

18. The apparatus of claim 10, wherein the pressure generator includes a compressed aerosol ejector for ejecting a jet of compressed aerosol towards the sample.

19. The apparatus of claim 10, further comprising a vacuum probe arranged beside the fluid beam to collect the fluid after it splitting from the sample surface.

* * * * *